(12) United States Patent
Lin et al.

(10) Patent No.: US 11,457,962 B2
(45) Date of Patent: Oct. 4, 2022

(54) FEMUR FIXATION DEVICE

(71) Applicant: DOUBLE MEDICAL TECHNOLOGY INC., Fujian (CN)

(72) Inventors: Zhixiong Lin, Fujian (CN); Qiang Long, Fujian (CN); Daohai Jiang, Fujian (CN); Meng Wang, Fujian (CN); Guixiong Fan, Fujian (CN); Chongbing Liu, Fujian (CN); Da Zeng, Fujian (CN)

(73) Assignee: DOUBLE MEDICAL TECHNOLOGY INC., Fujian (CN)

( * ) Notice: Subject to any disclaimer, the term of this patent is extended or adjusted under 35 U.S.C. 154(b) by 973 days.

(21) Appl. No.: 16/307,163

(22) PCT Filed: Jul. 25, 2018

(86) PCT No.: PCT/CN2018/097055
§ 371 (c)(1),
(2) Date: Dec. 5, 2018

(87) PCT Pub. No.: WO2019/024741
PCT Pub. Date: Feb. 7, 2019

(65) Prior Publication Data
US 2021/0220028 A1    Jul. 22, 2021

(30) Foreign Application Priority Data
Aug. 3, 2017  (CN) .......................... 201710657145.2

(51) Int. Cl.
*A61B 17/74* (2006.01)
*A61B 17/86* (2006.01)

(52) U.S. Cl.
CPC ........ *A61B 17/744* (2013.01); *A61B 17/8635* (2013.01)

(58) Field of Classification Search
CPC .............. A61B 17/744; A61B 17/8635; A61B 17/7283; A61B 17/742; A61B 17/844;
(Continued)

(56) References Cited

U.S. PATENT DOCUMENTS 4,978,350 A * 12/1990 Wagenknecht .... A61B 17/8635
411/387.7
8,491,584 B1 * 7/2013 Fagan ................ A61B 17/7266
606/64

(Continued)

FOREIGN PATENT DOCUMENTS

CN    201624765 U    11/2010
CN    103327918 A    9/2013
(Continued)

OTHER PUBLICATIONS

International Search Report (ISR) dated Oct. 26, 2018 for Application No. PCT/CN2018/097055.
(Continued)

*Primary Examiner* — Jan Christopher L Merene
*Assistant Examiner* — Anna V. Little
(74) *Attorney, Agent, or Firm* — Ladas & Parry LLP

(57) ABSTRACT

A femur fixation device includes an intramedullary nail having along its longitudinal axis a proximal portion, a distal portion and a lateral through hole extending through the proximal portion; and a hip screw capable of passing through the lateral through hole. An axis of the lateral through hole intersects the longitudinal axis at a first inclination angle. The proximal portion includes a first through hole. The first through hole is provided with a detachable positioning bracket therein. A positioning protrusion is defined at a lower end of one side of the positioning bracket. A line connecting the positioning protrusion and corresponding end points on a sidewall of the positioning bracket
(Continued)

intersects the longitudinal axis at a second inclination angle. An outer surface of the hip screw is provided with a positioning groove. A tail nail is disposed in the first through hole.

5 Claims, 6 Drawing Sheets

(58) Field of Classification Search
CPC ..... A61B 17/8655; A61B 17/84; A61B 17/86; A61B 17/863; A61B 17/72; A61B 17/74; Y10T 403/602; Y10T 403/599; F16B 19/109; F16B 21/18; F16B 21/186; F16B 21/125; F16B 31/02; F16B 13/0808
USPC .................................................. 606/300–321
See application file for complete search history.

(56) References Cited

U.S. PATENT DOCUMENTS

| | | | | |
|---|---|---|---|---|
| 2004/0068261 | A1* | 4/2004 | Fourcault | A61B 17/863 606/67 |
| 2005/0143739 | A1* | 6/2005 | Shinjo | A61B 17/744 606/62 |
| 2007/0233100 | A1* | 10/2007 | Metzinger | A61B 17/748 606/62 |
| 2007/0288017 | A1* | 12/2007 | Kaup | A61B 17/7241 606/62 |
| 2008/0140077 | A1* | 6/2008 | Kebaish | A61B 17/744 606/65 |
| 2009/0198237 | A1* | 8/2009 | Downey | A61B 17/744 606/62 |
| 2010/0249781 | A1* | 9/2010 | Haidukewych | A61B 17/7241 606/62 |
| 2011/0288599 | A1* | 11/2011 | Michielli | A61B 17/863 606/305 |
| 2014/0058392 | A1* | 2/2014 | Mueckter | A61B 17/7233 606/64 |
| 2017/0202584 | A1 | 7/2017 | Hientzsch et al. | |

FOREIGN PATENT DOCUMENTS

| | | | |
|---|---|---|---|
| CN | 106073877 | A * | 11/2016 |
| CN | 106073877 | A | 11/2016 |
| CN | 106236234 | A | 12/2016 |
| CN | 107320168 | A | 11/2017 |
| WO | 2016/190842 | A1 | 12/2016 |

OTHER PUBLICATIONS

Espacenet English abstract of CN 107320168 A.
Espacenet English abstract of CN 106236234 A.
Espacenet English abstract of CN 201627465 U.
Espacenet English abstract of CN 106073877 A.
Espacenet English abstract of CN 103327918 A.

* cited by examiner

100

200

200

FEMUR FIXATION DEVICE

CROSS REFERENCE TO RELATED APPLICATIONS

The present application is an application under 35 U.S.C. 371 of International Application No. PCT/CN2018/097055 filed Jul. 25, 2018, which claims priority from Chinese Patent Application No. 201710657145.2 filed Aug. 3, 2017, the disclosures of each of which are hereby incorporated herein by reference in their entirety.

FIELD OF THE INVENTION

The present invention relates to a medical device, and more particularly, to a femur fixation device.

BACKGROUND OF THE INVENTION

In terms of medicine, femur fracture is a disease in which a femur of a human body is broken partially or entirely due to injury. The femur fracture is difficult to recover. The fracture is very painful and difficult in moving and needs a long time to recover. The treatment of femur fracture must follow the three basic principles of reduction, fixation, and functional exercise. The reduction is to relocate the fracture caused already-misplaced femur fracture portion to its normal position as close as possible to restore the support function of the femur. To hold the skeletal structure after corrective reduction in place, a femur fracture treatment device or a femur fixation device is usually used.

Femur fracture usually occurs in the femoral neck and trochanteric regions. Typically, the trochanteric and subtrochanteric femur fracture are currently treated with an intramedullary nail having a lateral through hole for holding a bone fastener therein. The intramedullary nail is assembled in the medullary cavity of the femur to partially prevent the torsion of the fracture portion. A hip screw passes through the lateral through hole of the intramedullary nail, then the neck of the femur and finally enters the femur. The hip screw is generally rotatably inserted into the femur, and after installation, the intramedullary nail and the hip screw cannot rotate relative to each other. To this end, it is common to provide a positioning bolt in the intramedullary nail to fix the hip screw which passes through the lateral through hole to prevent relative movement or rotation between the intramedullary nail and the hip screw, or to make a hip screw of non-circular configuration to prevent rotation of itself, but these measures still fail to completely suppress the rotation, lateral movement and the like of the fracture portion. Further, subject to long-term external force in use, the positioning part is twisted and loosened, which easily causes rotation and axial movement of the intramedullary nail, resulting in delayed bone healing process. Although some interlocking intramedullary nails have better axial and rotational fixation than other intramedullary nails, they are complicated in structure, inconvenient in installation and renders long operation time.

SUMMARY OF THE INVENTION

Based on this, it is necessary to provide a femur fixation device to overcome the problem of structural instability of a prior art femur fixation device during long-term use.

A femur fixation device, comprises: an intramedullary nail having along its longitudinal axis a proximal portion, a distal portion and a lateral through hole extending through the proximal portion; and a hip screw capable of passing through the lateral through hole. An axis of the lateral through hole intersects the longitudinal axis at a first inclination angle. The proximal portion includes a first through hole that extends along the longitudinal axis and communicates with the lateral through hole. The first through hole is provided with a detachable positioning bracket therein. A positioning protrusion is defined at a lower end of one side of the positioning bracket. A line connecting the positioning protrusion and corresponding end points on a sidewall of the positioning bracket intersects the longitudinal axis at a second inclination angle. An outer surface of the hip screw is provided with a positioning groove which is parallel to its own axis and against which the positioning protrusion of the positioning bracket may be pressed so as to hold the hip screw in place by the fixing of the positioning bracket. A tail nail which is detachably connected to the first through hole and is pressed against the positioning According to an embodiment, at an upper end of the positioning bracket, a limiting slot is defined radially along the intramedullary nail, and a limiting latch engaging the limiting slot is further disposed on the positioning bracket, and the limiting latch is detachably connected to an inner wall of the first through hole.

Preferably, an elastic spacer is disposed between the limiting slot and the limiting latch.

Preferably, one end of the tail nail is provided with a stud of a predetermined length, and the other end thereof is provided with a counterbore in cooperation with a screwing tool.

According to an embodiment, a distal end of the distal portion is provided with a blade portion of which the diameter from the distal end to the proximal end is gradually reduced by a predetermined value, and the distal portion is uniformly provided with four arc cutter slots in a surface thereof.

Preferably, the distal portion includes a second through hole extending from the lateral through hole to a top end of the blade portion along the longitudinal axis, and a first rounded rectangular through hole for reducing the self-weight is defined in the distal portion at one end of the arc cutter slot.

Preferably, a second rounded rectangular through hole for reducing the self-weight is defined in the arc cutter slot, and a circular through hole for reducing the self-weight is defined in both ends of the second rounded rectangular through hole.

Preferably, the first inclination angle may be in a range of 105°-135°, and an axis of the second through hole is at an angle which is in a range of 110°-140° with the lateral through hole.

According to an embodiment, the hip screw is provided with a third through hole extending along the axis thereof; one end of the hip screw is provided with a cutting blade portion of a circular contour cross-section, the cutting blade portion includes at least one cutting slot and a plurality of spiral blades formed at a top end of both side walls of the cutting slot, a cross-section of the cutting slot includes a pair of first arcs each of which runs from the spiral blade to the bottom of the slot and of each of which a circle center is located in a space defined by the cutting slot, and the pair of first arcs in the same cutting slot are connected by a second arc of which a circle center is located at a circle center of the cross-section of the cutting blade portion.

Preferably, the cutting blade portion is a straight blade, the cutting slot is parallel to the axis of the hip screw; and the quantity of the cutting slots is three and the cutting slots are uniformly distributed along the circular contour.

According to an embodiment, a third through hole is defined to pass through the hip screw; and one end of the hip screw is a cutting blade portion including three spiral blades.

Preferably, the cutting blade portion is provided with a plurality of circular holes, some circular holes are defined in the spiral blade of the blade portion, and the other circular holes laterally run across the third through hole.

According to an embodiment, a third through hole is defined to pass through the hip screw; one end of the hip screw is provided with a cutting blade portion, the cutting blade portion is a threaded structure, and a plurality of circular holes laterally extended to the third through hole is uniformly defined in the cutting blade portion.

According to an embodiment, a bottom surface of the positioning groove is of an arc-shape.

According to an embodiment, a plane which is parallel to the positioning groove has a third inclination angle with a top end surface of the hip screw.

Preferably, the third inclination angle is in a range of 105°-135°.

According to an embodiment, the first inclination angle is equal to the second inclination angle.

According to an embodiment, the detachable connection is a threaded connection.

Compared to prior art, the femur fixation device of the present invention has the following technical effects:

At first, the relative location between the intramedullary nail and the hip screw can be adjusted or fixed by engagement between the positioning protrusion and the positioning groove, such that the femur fixation device has a simple structure, flexible use and reliable fixation.

Secondly, the positioning bracket with the positioning protrusion is fixed by the detachable tail nail inside the intramedullary nail, such that the femur fixation device can be easily disassembled, and at the same time, the stability of the positioning bracket when being fixed can be ensured.

Because of the above advantages, the femur fixation device of the present invention does not rotate even if it is in a circular shape, and the large-area engagement between the positioning protrusion and the positioning groove makes the movement between the two difficult. It solves the problem of structural instability of a prior art femur fixation device during long-term use and avoids the impact of this problem on bone healing.

DETAILED DESCRIPTION OF THE INVENTION

Figure 1:
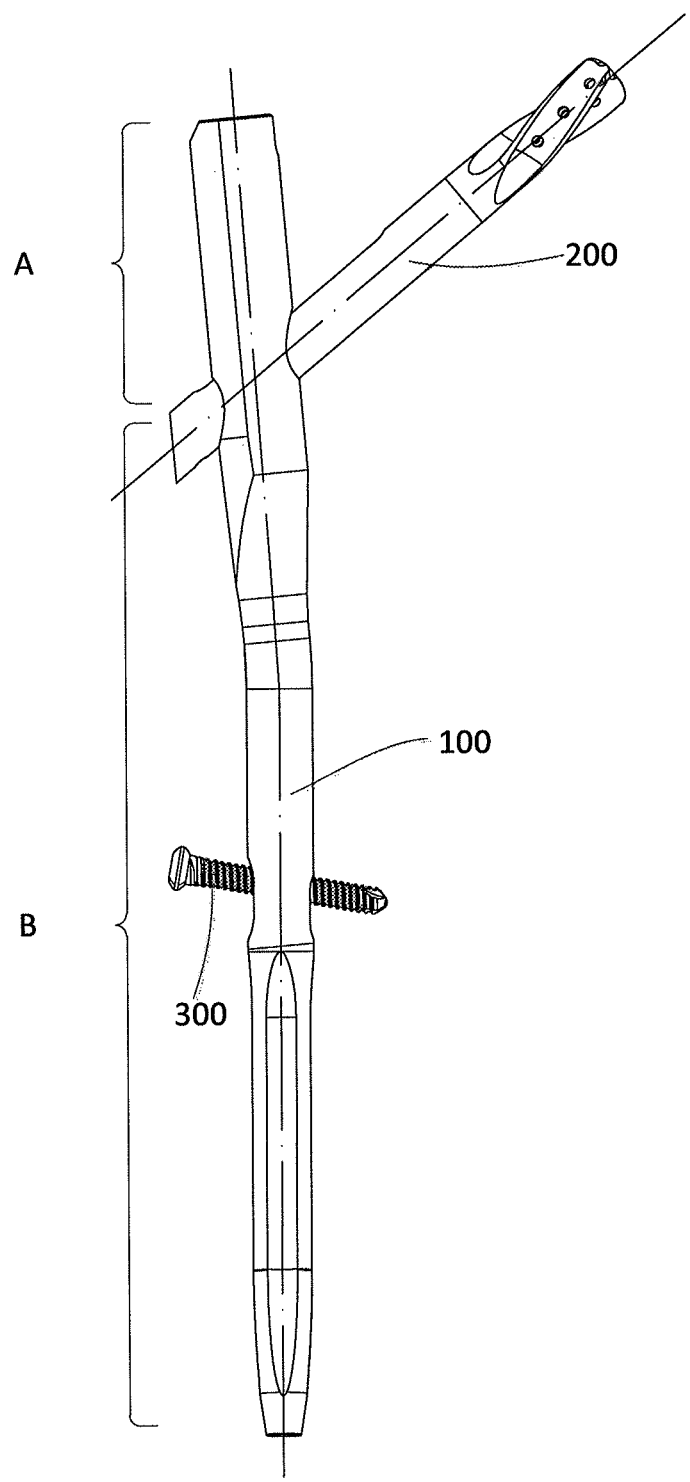
FIG. 1 shows a structural view of a femur fixation device according to an embodiment of the present invention.

Various exemplary embodiments of the present invention are further described below in conjunction with the accompanied drawings, wherein the same reference numerals refer to the same parts throughout the drawings. Further, if a detailed description of a known technique is unnecessary for showing the features of the present invention, it will be omitted.

Figure 2:
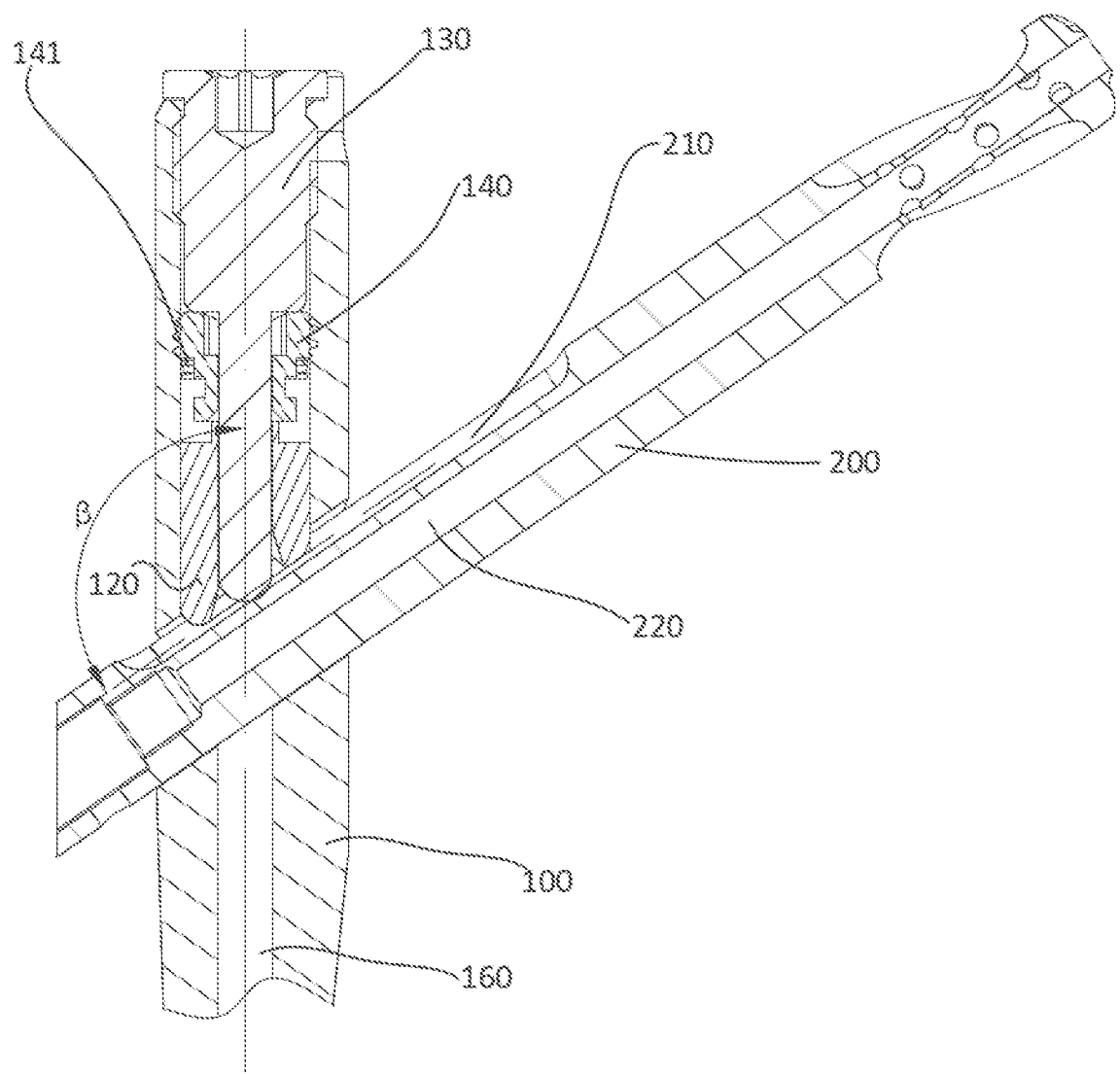
FIG. 2 shows a cross-sectional view of a femur fixation device according to an embodiment of the present invention.
Figure 3:
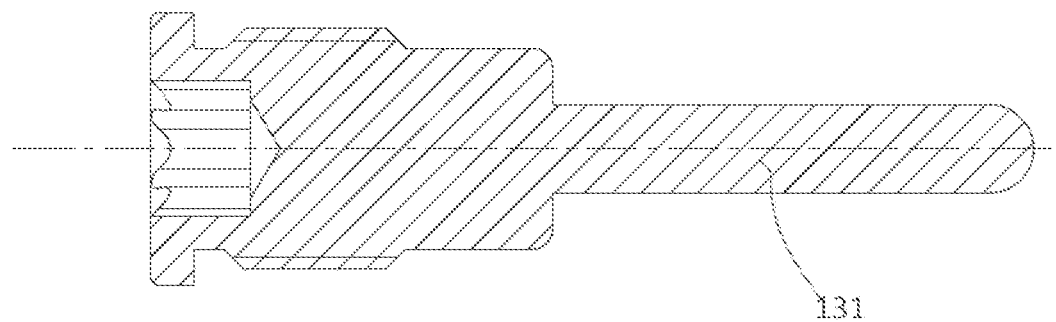
FIG. 3 shows a cross-sectional view of a tail nail according to an embodiment of the present invention.
Figure 12:
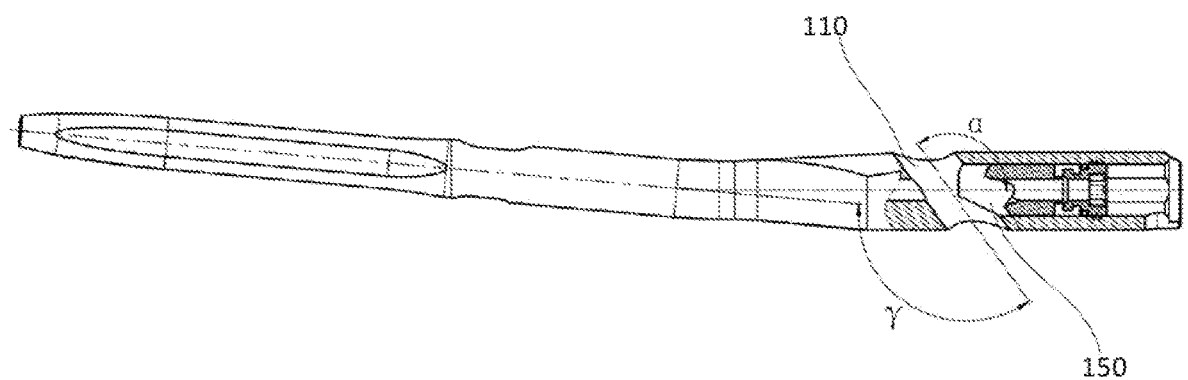
FIG. 12 shows a partial cross-sectional view of a hip screw according to an embodiment of the present invention.

Referring to FIGS. 1, 2 and 12, a femur fixation device of the present invention includes an intramedullary nail 100 and a hip screw 200. For the intramedullary nail 100, along its longitudinal axis, it includes a proximal portion A, a distal portion B and a lateral through hole 110 that extends through the proximal portion A. An axis of the lateral through hole 110 of the intramedullary nail 100 intersects the longitudinal axis of the proximal portion A at a first inclination angle $\alpha$, as shown in FIG. 12, according to the law of human ergonomics, the first inclination angle $\alpha$ may be in a range of 105°-135°, and preferably be 125°. The proximal portion A of the intramedullary nail 100 includes a first through hole 150 that extends along the longitudinal axis and communicates with the lateral through hole 110. The first through hole 150 is provided with a detachable positioning bracket 120 therein, and a positioning protrusion 121 is defined at a lower end of one side of the positioning bracket 120, and a line connecting the positioning protrusion and corresponding end points on a sidewall of the positioning bracket intersects the longitudinal axis at a second inclination angle. The positioning protrusion 121 may take many different forms such as two or more discontinuous or continuous form of certain length, and the line connecting the positioning protrusion 121 and corresponding end points on a sidewall of the positioning bracket may be deemed a top end connection of the positioning protrusion 121. The second inclination angle $\beta$ may be preferably equal to the first inclination angle $\alpha$. When the first inclination angle $\alpha$ and the second inclination angle $\beta$ are equal to each other, except the positioning bracket can abut into a positioning groove by itself, it also can abut into the positioning groove by other protruded portion which is opposite to the positioning protrusion, thus increasing contact area and stability, and making it easier to manufacture and assemble. As shown in FIG. 2, the hip screw 200 can pass through the lateral through hole 110, and an outer surface of the hip screw 200 is provided with the positioning groove 210 which is parallel to its own axis and against which the positioning protrusion 121 of the positioning bracket 120 be pressed so as to hold the hip screw 200 in place by the fixing of the positioning bracket 120. A tail nail 130 is disposed in the first through hole 150, as shown in FIGS. 2 and 3, the tail nail 130 is detachably connected to the first through hole 150 and is pressed against the positioning bracket 120. Additional use of the tail nail 130 instead of being directly and detachably connected to the first through hole 150 by the positioning bracket 120, is for the purposes of more stably securing the positioning bracket 120 into the first through hole 150 at a corresponding position. It should be noted that the detachable connection is preferably threaded connection. On one hand, the threaded connection facilitates standard manufacturing, and on the other hand, the threaded connection can well meet the requirements of stable connection. Preferably, the positioning bracket 120 and the tail nail 130 are threaded according to different specifications.

Figure 4:
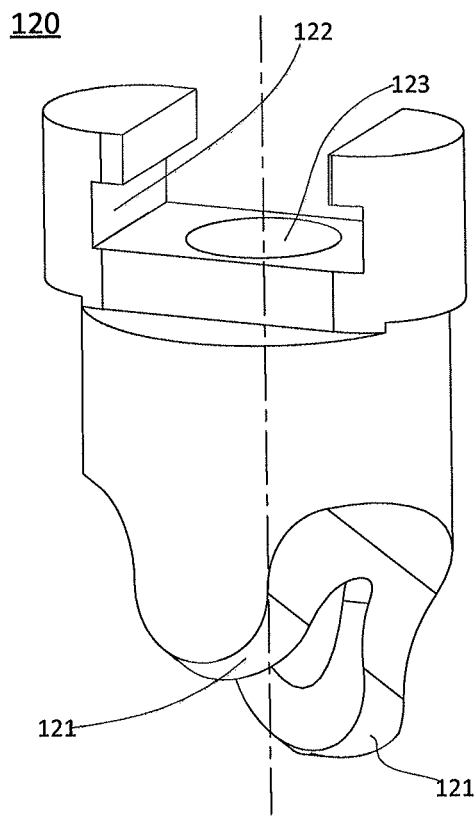
FIG. 4 shows a structural view of a positioning bracket according to an embodiment of the present invention.
Figure 5:
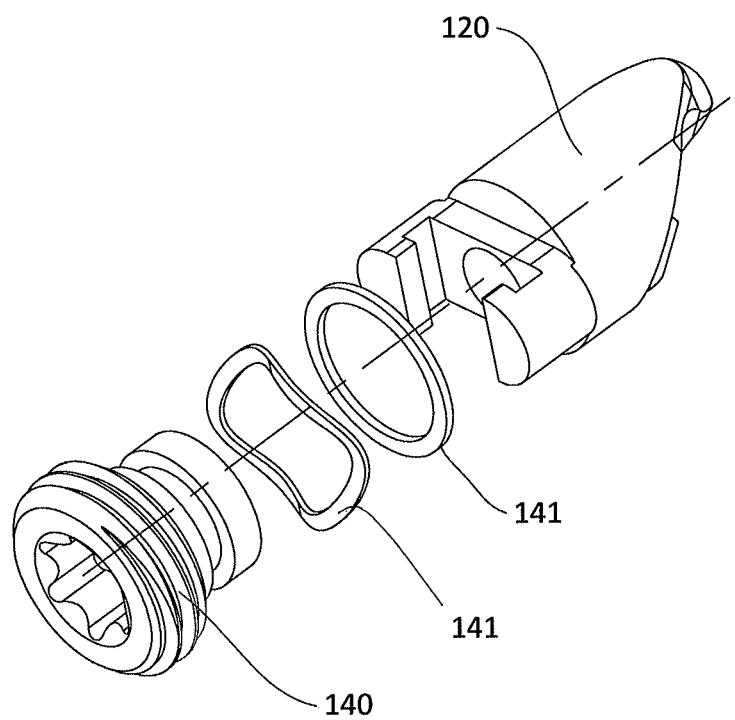
FIG. 5 shows a structural view of a positioning bracket in an assembling state according to an embodiment of the present invention.

As a preferred embodiment, as shown in FIG. 4, the positioning bracket 120 of the intramedullary nail 100 is further designed. At an upper end of the positioning bracket 120, a limiting slot 122 is defined radially along the intramedullary nail 100, and a limiting latch 140 engaging the limiting slot 122 is further disposed. As shown in FIG. 5, the limiting latch 140 is detachably connected to an inner wall of the first through hole 150, by means such as a threaded connection. A counterbore engaging a screwing tool is further disposed on a top end surface of the limiting latch 140. The limiting latch 140 is inserted into the limiting slot 122 along a diameter direction of the positioning bracket 120 to realize engagement between the limiting latch 140 and limiting slot 122, and convenient installation. At the same time, in order to reduce the weight of the positioning bracket 120, a through hole 123 can be defined to pass through the positioning bracket 120. More preferably, as shown in FIG. 5, an elastic spacer 141 is disposed between the limiting slot 122 and the limiting latch 140 aiming at a small amount of elastic movement of the positioning bracket 120. On one hand, various components are assembled together to form the femur fixation device before sale, and the position is predetermined before use to prevent the components of the device from loosening. It is also beneficial to improve the actual surgical installation efficiency, and allowance of a small amount of movement permits the major components of the femur fixation device to be located in advance precisely. On the other hand, in practical application of the device into a patient, there will be inevitable severe shocks. The elastic movement in a small amount allows certain elasticity to the post-operative skeletal system such that it will be more in compliance with the natural state of the human skeleton. More preferably, as shown in FIGS. 2 and 3, one end of the tail nail 130 is provided with a stud 131 of a predetermined length to facilitate the connection between the tail nail 130 and the limit latch 140. When the positioning bracket 120 is provided with the through hole 123, the stud 131 can also pass through the through hole 123 to be pressed against the positioning groove 210 of the hip screw 200, and the other end of the tail nail 130 is also provided with a counterbore for engaging with a generally used tool including a straight slot, a cross slot, a hexagonal slot or a star slot in cooperation with a screwing tool, to be driven by the screwing tool with ease.

Figure 6:
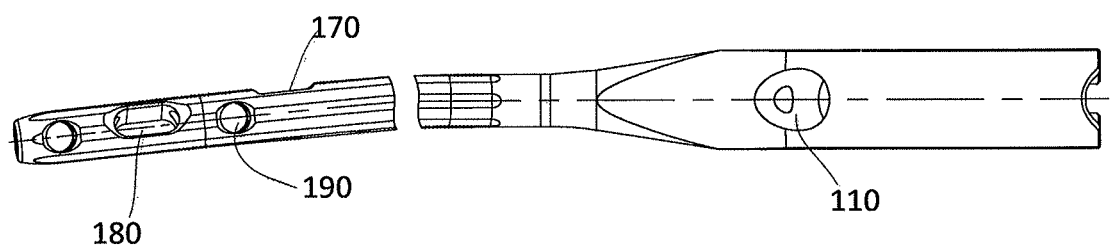
FIG. 6 shows a structural view of an intramedullary nail according to an embodiment of the present invention.

As a preferred embodiment, as shown in FIG. 6, a distal end of the distal portion B of the intramedullary nail 100 is provided with a blade portion of which the diameter from the distal end to the proximal end is gradually reduced by a predetermined value. The distal portion B is uniformly provided with four arc cutter slots in a surface thereof so as to make the intramedullary nail 100 easier to enter into the bone. Preferably, the distal portion B includes a second through hole 160 extending from the lateral through hole 110 to a top end of the blade portion along the longitudinal axis, as shown in FIG. 12, when the first inclination angle is set to 125°, the axis of the second through hole 160 is at an angle γ with the lateral through hole 110, and they angle is in a range of 110°-140°, and preferably is 130°. And a first rounded rectangular through hole 170 for reducing the self-weight is defined in the distal portion B at one end of the arc cutter slot. Of course, into the first rounded rectangular through hole 170, a lateral positioning screw 300 (shown in FIG. 1) can also be inserted according to actual needs to hold the intramedullary nail 100 in place. More preferably, in order to simplify the structure of the intramedullary nail 100, the weight of the intramedullary nail 100 is minimized while keeping predefined toughness for the intramedullary nail 100 by providing a second rounded rectangular through hole 180 in the arc cutter slot. A circular through hole 190 for reducing the self-weight is provided at both ends of the second rounded rectangular through hole 180.

Figure 7:
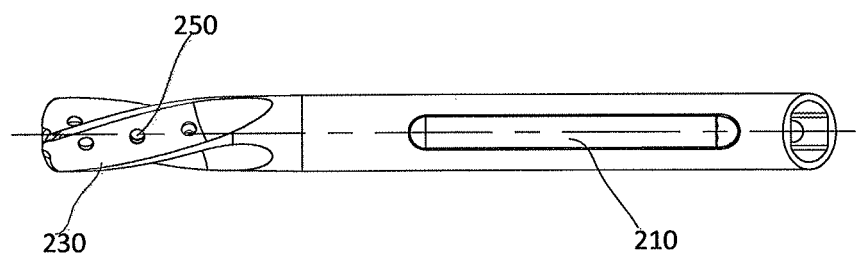
FIG. 7 shows a structural view of a hip screw according to an embodiment of the present invention.

As a preferred embodiment, as shown in FIG. 7, a third through hole 220 is defined to pass through the hip screw 200, and the hip screw 200 has a cutting blade portion at one end thereof, and the cutting blade portion includes three spiral blades 230.

Figure 8:
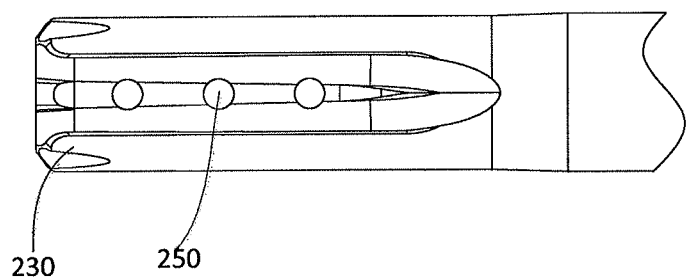
FIG. 8 shows a structural view of a hip screw according to another embodiment of the present invention.
Figure 9:
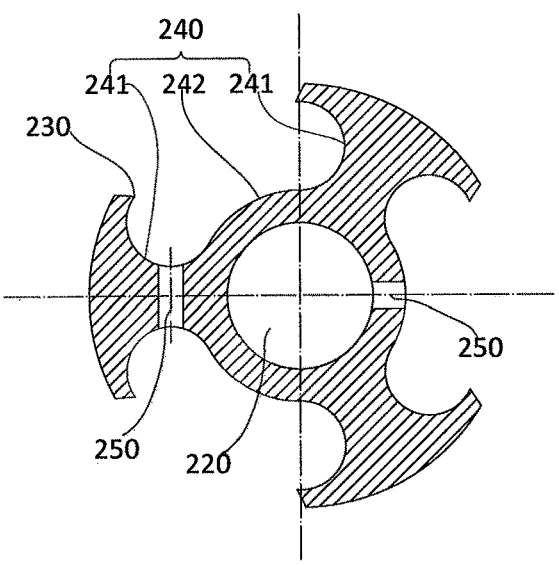
FIG. 9 shows a cross-sectional view of a hip screw according to another embodiment of the present invention.
Figure 10:
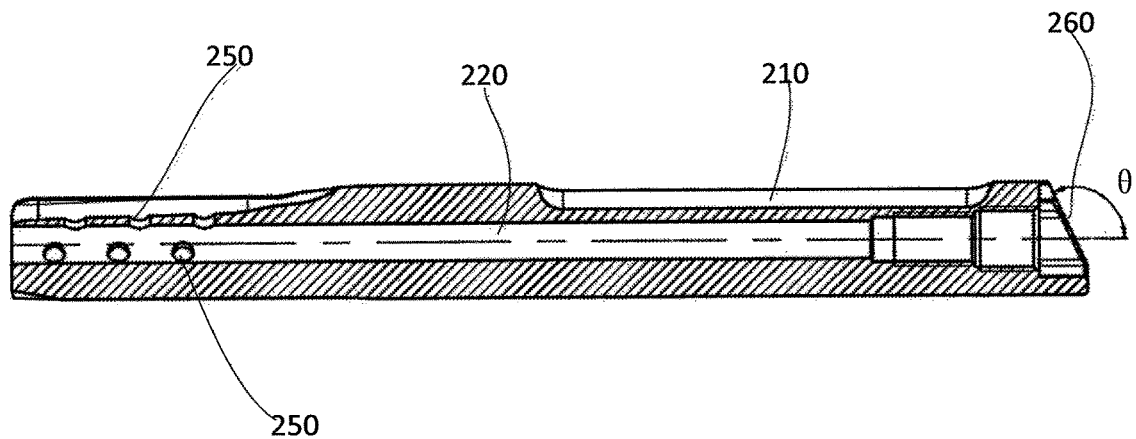
FIG. 10 shows a cross-sectional view of a hip screw according to another embodiment of the present invention.

As another preferred embodiment, as shown in FIG. 8, the hip screw 200 is also provided with a third through hole 220 extending along the axis thereof. One end of the hip screw 200 is provided with a cutting blade portion of a circular contour cross-section, and the cutting blade portion includes at least one cutting slot 240 and a spiral blade 230 formed at the top end of both side walls of the cutting slot 240, as shown in FIG. 9, a cross-section of the cutting slot 240 includes a pair of first arcs 241 each of which runs from the spiral blade 230 to the bottom of the cutting slot and of each of which a circle center is located in a space defined by the cutting slot 240, and the pair of first arcs 241 in the same cutting slot 240 are connected by a second arc 242 of which a circle center is located at a circle center of the cross-section of the cutting blade portion. That is to say, the cross-section of the cutting slot 240 is composed of two first arcs 241 and one second arc 242, the second arc 242 is respectively connected to the two first arcs 241, the circle center of the two first arcs 241 are at the same side of a line, and the circle center of the second arc 242 is at the other side of the line. The circle center of the second arc 242 coincides with the circle center of the cross-section of the blade structure, and the radii of the two arcs are different from each other. Preferably, the cutting blade portion is a straight blade, the cutting slot 240 is parallel to the axis of the hip screw 200, and the quantity of the cutting slots 240 is three and the cutting slots are uniformly distributed along a circular contour. In an ideal state the hip screw 200, should be embedded in an object and be kept stationary at least in the radial direction of the hip screw 200. That is to say, the hip screw 200 will not be rotated around an axis when external force applies thereto, and the cutting blade portion has a small opening and a relatively large internal cavity, so that after the hip screw is embedded in the object, the cutting slot 240 is filled with much material of the object, which can generate great resistance to the rotation of the cutter and avoid the radial positional change. More preferably, the cutting blade portion is provided with a plurality of circular holes 250, some circular holes 250 are defined in the spiral blade 230 of the blade portion, and the other circular holes 250 are laterally run across the third through hole 220.

Figure 11:
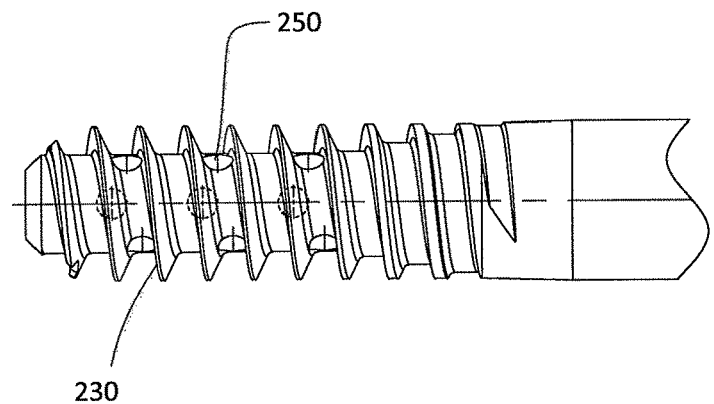
FIG. 11 shows a structural view of a hip screw according to another embodiment of the present invention.

There is also a preferred embodiment, as shown in FIG. 11. a third through hole 220 is also defined to pass through the hip screw 200, and here the cutting blade portion is of a threaded structure, and a plurality of circular holes 250 laterally extended to the third through hole 220 is uniformly defined in the cutting blade portion. The cutting blade portion of the threaded structure is not only easy to manufacture, but also has the advantage of being easily inserted into the bone.

On one hand, the circular holes 250 provided in the above embodiment can reduce the weight of the hip screw 200 making it lighter while keeping the structure stable, and on the other hand, the intra-bone material separated by the spiral blade 230 can be exchanged through the circular holes, thereby reducing disturbance of the device to substances in the bone. The circular holes passing through the third through hole 220 can also serve as cement holes, which are mainly used in case of osteoporosis in the elderly, through which the bone cement is injected into the femur to enhance the stability of the hip screw 200.

As the positioning groove 210 is a groove defined in a curved surface, there must be a plane defined by a length direction and width direction of the positioning groove 210 and parallel to the positioning groove 210. As a preferred embodiment, the plane has a third inclination angle θ with a top end surface of the connecting portion, and the third inclination angle θ is in a range of 105°–135°. That is to say, when the hip screw 200 is in the assembled position, the top end surface 260 can be nearly parallel or parallel to the axis of the intramedullary nail 100. Such an arrangement makes the femur fracture treatment device more closely match the natural bone structure of the human body, and also makes the femur fracture treatment device more compact, and preferably the third inclination angle θ is 115c. In addition, a bottom surface of the positioning groove 210 may be provided in various shapes, for example, it may have a rectangular shape, a triangular shape or an arc shape, and it preferably has an arc-shape, as the arc-shaped bottom surface makes the contact area between a plug body provided on the intramedullary nail 100 and the positioning groove 210 larger, so that the connection structure of the two is more stable. More preferably, suitably rounded corners are provided on each edge of the positioning slot 210 to make it easier to engage a mating structure such as the plug body.

While some exemplary embodiments of the present invention have been shown in the foregoing, it will be understood by those skilled in the art that variations of the exemplary embodiments may be made without departing from the spirit and scope of the invention, and the scope of the invention is defined by the claims and their equivalents.

The invention claimed is:

1. A femur fixation device, comprising
(a) an intramedullary nail having a longitudinal axis and, along the longitudinal axis, a proximal portion, a distal portion and a lateral through hole extending through the proximal portion;
(b) a hip screw capable of passing through the lateral through hole, the lateral through hole having an axis that intersects the longitudinal axis of the intramedullary nail at a first inclination angle; the proximal portion of the intramedullary nail including a first through hole that extends along the longitudinal axis of the intramedullary nail and communicates with the lateral through hole;
(c) a positioning bracket detachably disposed within the first through hole; the detachable positioning bracket comprising a positioning protrusion at a lower end of one side of the positioning bracket and a limiting slot defined radially at an upper end of the positioning bracket; the positioning protrusion and corresponding end points on a sidewall of the positioning bracket defining a line that intersects the longitudinal axis at a second inclination angle; the hip screw having an axis and comprising an outer surface with a positioning groove which is parallel to the axis of the hip screw and against which the positioning protrusion of the positioning bracket is pressable to hold the hip screw in place with the positioning bracket;
(d) a tail nail detachably connectable to the first through hole and pressable against the positioning bracket with the positioning bracket disposed in the first through hole at the upper end of the positioning bracket;
(e) a limiting latch disposable on the positioning bracket, engageable in the limiting slot and detachably connectable to an inner wall of the first through hole; and
(f) an elastic spacer disposable between the limiting slot and the limiting latch with the limiting latch engaged in the limiting slot.

2. The femur fixation device of claim 1, wherein the tail nail comprises a first end with a stud of a predetermined length, and a second end with a counterbore in cooperation with a screwing tool.

3. A femur fixation device, comprising
(a) an intramedullary nail having a longitudinal axis and, along the longitudinal axis, a proximal portion, a distal portion and a lateral through hole extending through the proximal portion;
(b) a hip screw capable of passing through the lateral through hole, the lateral through hole having an axis that intersects the longitudinal axis of the intramedullary at a first inclination angle; the proximal portion of the intramedullary nail including a first through hole that extends along the longitudinal axis of the intramedullary nail and communicates with the lateral through hole;
(c) a positioning bracket detachably disposed within the first through hole; the detachable positioning bracket comprising a positioning protrusion at a lower end of one side of the positioning bracket and a limiting slot defined radially at an upper end of the positioning bracket; the positioning protrusion and corresponding end points on a sidewall of the positioning bracket defining a line that intersects the longitudinal axis at a second inclination angle; the hip screw having an axis and comprising an outer surface with a positioning groove which is parallel to the axis of the hip screw and against which the positioning protrusion of the positioning bracket is pressable to hold the hip screw in place with the positioning bracket;
(d) a tail nail detachably connectable to the first through hole and pressable against the positioning bracket with the positioning bracket disposed in the first through hole at an upper end of the positioning bracket; and
e) a limiting latch disposable on the positioning bracket, engageable in the limiting slot and detachably connectable to an inner wall of the first through hole;
wherein the hip screw comprises a third through hole extending along the axis of the hip screw; the hip screw being provided with a circular contour cross-section having a cutting blade portion, the cuttirg blade portion including at least one cutting slot having two side walls and a plurality of spiral blades formed at a top end of each of the side walls, the at least one cutting slot having a cross section including a pair of first arcs each of which runs from the spiral blades to the bottom of the at least one cutting slot and each of which has a circular center located in a space defined by the at least one cutting slot, wherein the pair of first arcs in the cutting slot are connected by a second arc having a circle center located at a circle center of the circular contour cross-section.

4. The femur fixation device of claim 3, comprising three cutting slots, including the at least one cutting slot, the three cutting slots being uniformly distributed along the circular contour, wherein the cutting blade portion is a straight blade, and the cutting slots are parallel to the axis of the hip screw.

5. The femur fixation device of claim 3, wherein the cutting blade portion is provided with a plurality of circular holes, including a first plurality of circular holes in the spiral blade of the blade portion, and a second plurality of circular holes running laterally across the third through hole.

\* \* \* \* \*